(12) United States Patent  
Tanaka et al.

(10) Patent No.: US 6,777,111 B1  
(45) Date of Patent: Aug. 17, 2004

(54) ELECTRO LUMINESCENT ELEMENT

(75) Inventors: Hiromitsu Tanaka, Aichi-ken (JP); Makoto Mouri, Aichi-ken (JP); Hisato Takeuchi, Aichi-ken (JP); Shizuo Tokito, Aichi-ken (JP)

(73) Assignee: Kabushiki Kaisha Chuo Kenkyusho, Aichi-gun (JP)

( * ) Notice: Subject to any disclaimer, the term of this patent is extended or adjusted under 35 U.S.C. 154(b) by 72 days.

(21) Appl. No.: 09/632,348

(22) Filed: Aug. 3, 2000

(30) Foreign Application Priority Data

Aug. 4, 1999 (JP) .......................................... 11-221653

(51) Int. Cl.$^7$ ............................................... H05B 33/12
(52) U.S. Cl. ....................... 428/690; 428/917; 313/504; 313/506
(58) Field of Search ................................ 428/690, 917; 313/504, 506; 257/40, 103

(56) References Cited

U.S. PATENT DOCUMENTS

| | | | |
|---|---|---|---|
| 5,281,489 A | * 1/1994 | Mori et al. ................. | 428/690 |
| 5,420,351 A | * 5/1995 | Suzuki et al. ............... | 564/308 |
| 5,554,450 A | 9/1996 | Shi et al. .................... | 428/690 |
| 5,605,795 A | 2/1997 | Bronstein ..................... | 435/6 |
| 5,707,559 A | 1/1998 | Schaap et al. .............. | 252/700 |
| 5,817,430 A | 10/1998 | Hsieh ......................... | 428/690 |
| 5,945,502 A | 8/1999 | Hsieh et al. ................ | 528/101 |

FOREIGN PATENT DOCUMENTS

| | | | |
|---|---|---|---|
| JP | 10-053759 | 2/1998 | |
| WO | WO 99/19419 | * 4/1999 | |
| WO | WO 00/03565 | * 1/2000 | |

* cited by examiner

*Primary Examiner*—Marie Yamnitzky  
(74) *Attorney, Agent, or Firm*—Oblon, Spivak, McClelland, Maier & Neustadt, P.C.

(57) ABSTRACT

In order to provide an electro luminescent element with high heat endurance and low crystallinity using functional molecules having functions of hole transporting, luminescence, and electron transporting, an electro luminescent element according to the present invention comprises one or more organic compound layers 14 between a first electrode 12 and a second electrode 16, wherein at least one of the organic compound layers 14 is a condensed ring compound derivative represented by the following chemical formula,

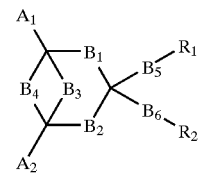

in which A1 and A2 represent substituents, B1 through B6 represent directly connected or di functional substituents, and R1 and R2 represent functional units having each of the functions of hole transporting, luminescence, and electron transporting, such as triphenylamine, coumarin, and oxadiazole derivative.

8 Claims, 1 Drawing Sheet

ELECTRO LUMINESCENT ELEMENT

BACKGROUND OF THE INVENTION

1. Field of the Invention

Figure 1:
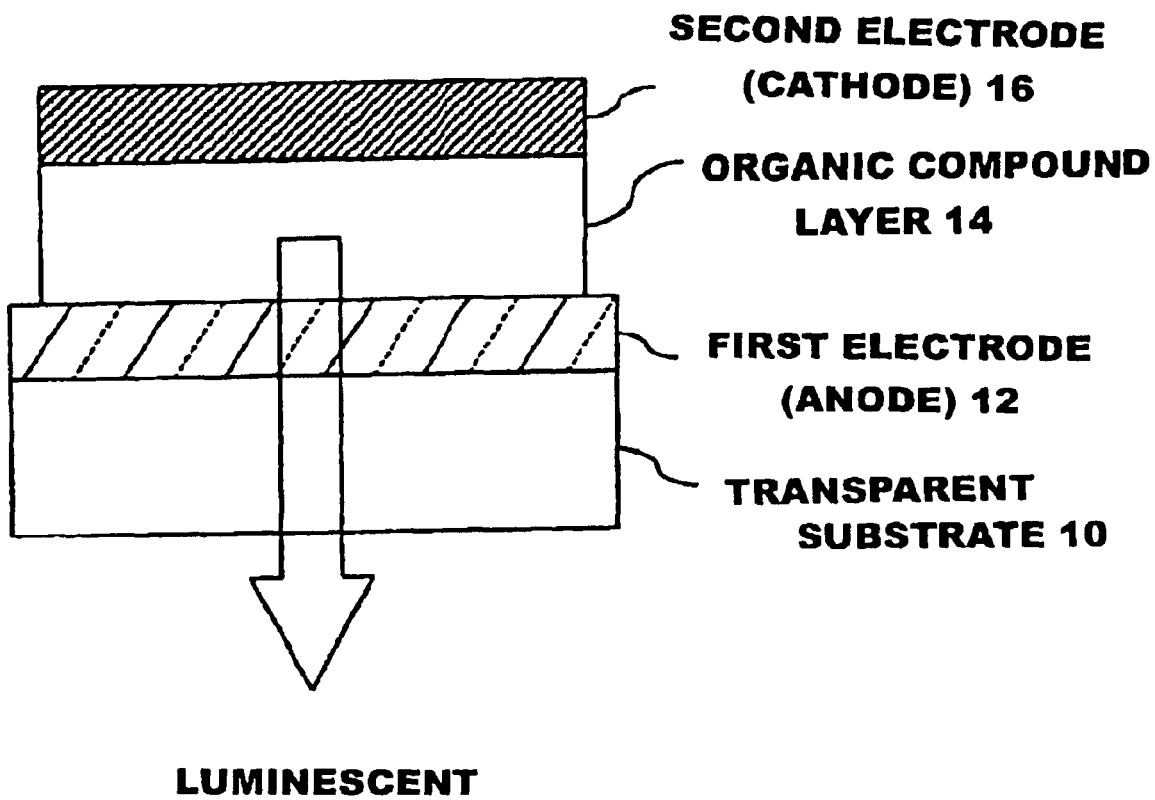

The present invention relates to an electro luminescent element and in particular to improved organic compound materials for use in an electro luminescent element.

2. Description of the Related Art

An electro luminescent element is constructed by layering, in order, a transparent first electrode (such as, for example, an ITO), an organic compound layer with an organic compound having strong fluorescence, and a second electrode formed of a metal (such as, for example, Mg). The organic compound layer is constructed by layering a hole transporting molecule, a luminescence molecule, and an electron transporting molecule in order, and emits light when electric field is applied between the pair of electrodes. In other words, when holes are injected from the first electrode and electrons are injected from the second electrode, the injected holes and electrons move through the organic compound layer and collide with each other to recombine and vanish. By this recombination, energy is generated which is then used to produce an excited state of the luminescence molecule so that the element emits fluorescent light.

Such an electro luminescent element has advantageous characteristics over other display elements such as a liquid crystal, a plasma display, or an inorganic electro luminescent element, such as no limitation on the angle of view, capability of being driven at a low voltage, and rapid response.

As a hole transporting material of the organic electro luminescent element, a TPD (tetraphenylbenzidin) which has been proposed by Tang et al. is widely in use. Because TPD has superior hole transporting ability, an organic electro luminescent element using TPD as a hole transporting molecule such as, for example, an element having a structure, [ITO/TPD (60 nm)/Alq3 (60 nm)/Mg:Ag (1500 nm)], has an excellent initial performance with a maximum luminance reaching few tens of thousand cd/m$^2$.

PBD (t-butylbiphenylylphenyloxadiazole) has been proposed as an electron transporting material by Tsutsui et al. PBD is a material having a high electron transporting ability and, at the same time, is a blue luminescence material of high luminance.

However, even though each of the conventional hole transporting, luminescence, and electron transporting molecules have good electric functionality characteristics, they also suffer problems of high crystallinity and low heat endurance. Because of these disadvantages, most of these materials cannot be used as materials for an organic electro luminescent element. For example, even though TPD (tetraphenylbenzidin) and triphenylamine are materials with good hole transporting ability, they exhibit high crystallinity and low heat endurance, which causes crystallization leading to element breakdown within one month after forming an element.

Similarly, even though PBD (t-butylbiphenylylphenyloxadiazole) is a material with good electron transporting ability, it has a fast crystallization, leading to an element breakdown within one week of forming a film.

SUMMARY OF THE INVENTION

The present invention is conceived to solve the above problems and an object of the present invention is to provide an electro luminescent element using functional molecules each having a function of hole transporting ability, luminescence, and electron transporting ability, the electro luminescent element having high heat endurance and low crystallinity.

According to one aspect of the present invention, in order to achieve the above object, there is provided an electro luminescent element comprising one or more organic compound layers between the electrodes, wherein at least one of the organic compound layers is a condensed ring compound derivative represented by a chemical formula,

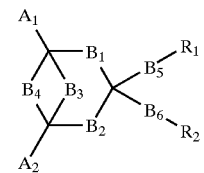

in which A1 and A2 represent substituents, B1 through B6 represent directly combined or 2 functional substituents, and R1 and R2 represent functional units such as triphenylamine, coumarin, and oxadiazole derivative, etc., with each of the functions of hole transporting ability, luminescence, and electron transporting ability.

With the structure defined above, by using a condensed ring compound derivative for each of the functional molecules of hole transport, luminescence, and electron transport, low crystallinity and high heat endurance which are preferable characteristics of an organic electro luminescent element can be added while maintaining good electric characteristics. This is because the condensed ring compound has a non-planer structure and reduced symmetry of the molecule shape. Because of these factors, the crystallinity of the molecule is reduced and the movability of the molecule can be reduced by introducing a molecular skeleton of a rigid condensed ring compound, resulting in improved heat endurance.

According to a second aspect of the present invention, there is provided an electro luminescent element with the structure of the first aspect, wherein each of the functional units R1 and R2 is selected from the group consisting of triphenylamine, coumarin, and oxadiazole derivative.

According to a third aspect of the present invention, there is provided an electro luminescent element with the structure of the first aspect, wherein the condensed ring compound derivative is distributed among host materials and the host material is further layered in the organic compound layer.

According to a fourth aspect of the present invention, there is provided an electro luminescent element with the structure of the first aspect, wherein the condensed ring compound derivative has a structure represented by one of the following chemical formulae (a)~(l):

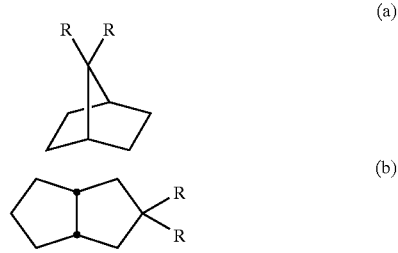

-continued
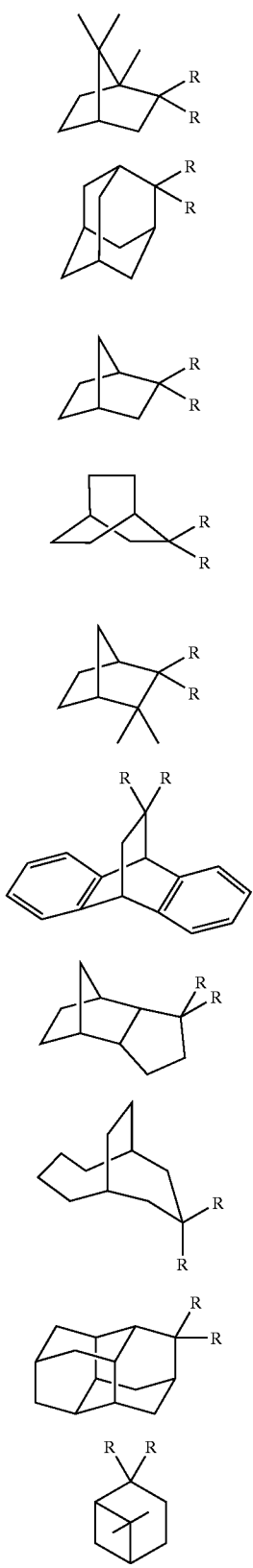
in which R represents the functional units.
According to a fifth aspect of the present invention, there is provided an electro luminescent element with the structure of the first aspect, wherein the functional unit has a structure represented by one of the following chemical formulae (r1)~(r22):
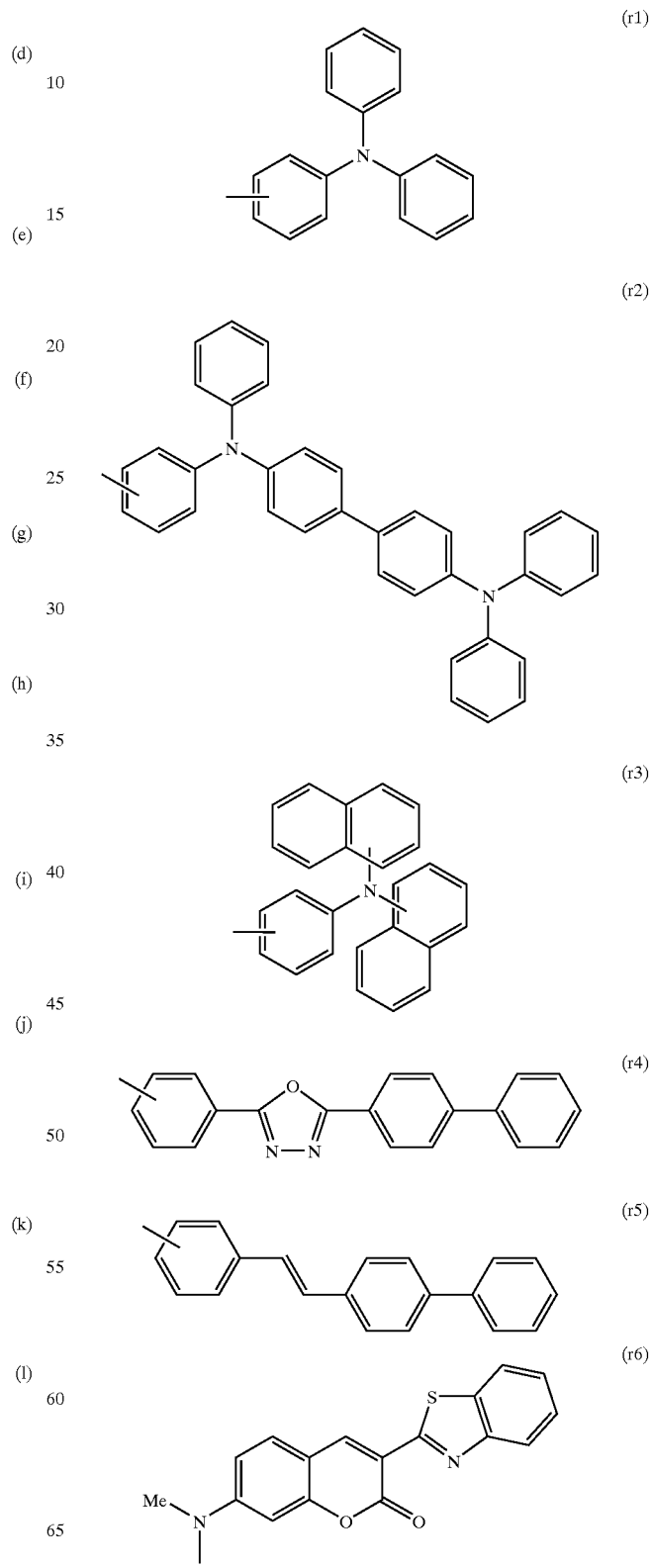

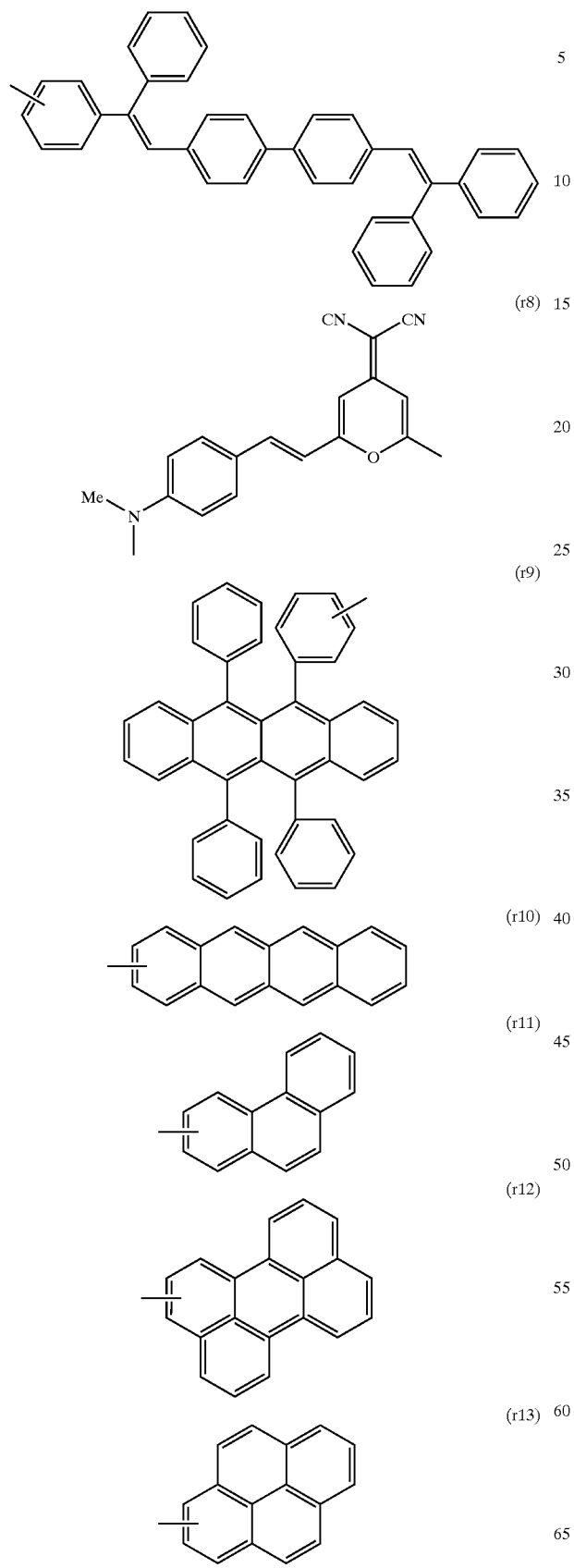
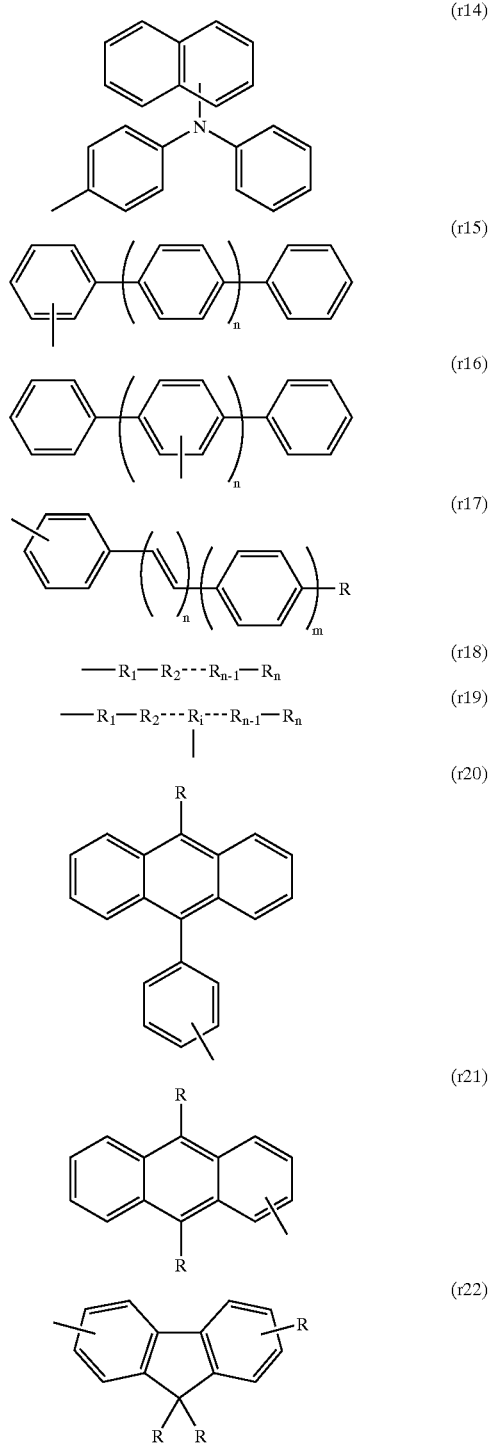

in which n, m, and i represent integers, R represents saturated hydrocarbon from C1 through C30, an isomer thereof, or an aromatic compound.

According to a sixth aspect of the present invention, there is provided an electroluminescent element with the structure of the fifth aspect, wherein R is aromatic and is selected from the group consisting of phenyl, naphthyl, indenyl, fluorenyl, phenanthryl, anthranyl, pyrenyl, chrysenyl, naphthacenyl, benzophenanthrenyl, furanyl, thiophenyl, pyrrolyl, oxazolyl, isoxazolyl, pyrazolyl, triazolyl, furazanyl, pyridyl, oxazyl, morpholyl, thiazyl, pyridazyl, pyrimidyl, pyrazyl, triazyl, benzofuryl, isobenzofuryl, benzothiophenyl, indolyl, isoindolyl, benzoxazolyl, benzothiazolyl, benzoimidazolyl, chromenyl, quinolyl, isoquinolyl, cinnolyl, phthalazyl, quinazolyl, quinoxalyl, dibenzofuril, carbazolyl, xanthenyl, acridinyl, phenanthridinyl, phenanthryl, phenazinyl, phenoxazinyl, thianthrenyl, indolizinyl, quinolizinyl, naphthyridinyl, purinyl, oxadiazolyl, and oxathiazolyl.

According to a seventh aspect of the present invention, there is provided an electro luminescent element comprising one or more organic compound layers between the electrodes, wherein at least one of the organic compound layers is an adamantane derivative represented by the following chemical formula,

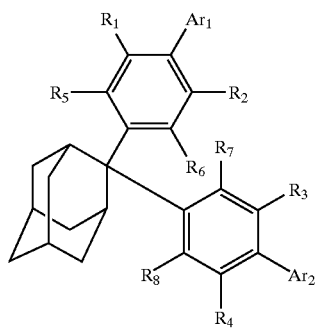

in which R1 through R8 represent substituents, and Ar1 and Ar2 represent functional units having hole transporting ability, luminescence, and electron transporting ability.

According to the structure mentioned above, the organic compound layer is a compound having the adamantane derivative as its main skeleton and the adamantane derivative is a rigid molecule with a good heat endurance. By introducing substituents on R1 through R8, rotation around the connecting axes between the adamantane and benzene ring and between the benzene ring and the substituent unit are constrained, so that the movability and internal rotation of the molecule is reduced, resulting in improved heat endurance compared to a case without substituents.

According to an eighth aspect of the present invention, there is provided an electro luminescent element with the structure of the seventh aspect, wherein the adamantane derivative is distributed among host materials and the host material is further layered in the organic compound layers.

According to a ninth aspect of the present invention, there is provided an electro luminescent element with the structure of the seventh aspect, wherein the substituents R1 through R8 are substituted with a functional group including alkyl group, aryl group, allyl group, alkene group, alkyne group, alkoxy group, hydroxyl group, hydroxylate group, thiocarboxy group, dithiocarboxy group, sulfo group, sulfino group, sulfeno group, oxycarbonyl group, haloformyl group, carbamoyl group, hydrazinocarbonyl group, amidino group, cyano group, isocyano group, cyanato group, thiocyanato group, isothiocyanato group, formyl group, oxo group, thioformyl group, thioxo group, mercapto group, amino group, imino group, hydrazino group, aryloxy group, sulfide group, halogen group, nitro group, and silyl group.

According to a tenth aspect of the present invention, there is provided an electro luminescent element with the structure of the seventh aspect, wherein each of the functional units Ar1 and Ar2 has an aryl skeleton as a basic skeleton.

According to an eleventh aspect of the present invention, there is provided an electro luminescent element with the structure of the tenth aspect, wherein the aryl skeleton is selected from the group consisting of phenyl, naphthyl, and phenanthryl.

According to a twelfth aspect of the present invention, there is provided an electro luminescent element with the structure of the tenth aspect, wherein the functional units Ar1 and Ar2 is further substituted by functional groups including alkyl group, aryl group, allyl group, alkene group, alkyne group, alkoxy group, hydroxyl group, hydroxylate group, thiocarboxy group, dithiocarboxy group, sulfo group, sulfino group, sulfeno group, oxycarbonyl group, haloformyl group, carbamoyl group, hydrazinocarbonyl group, amidino group, cyano group, isocyano group, cyanato group, isocyanato group, thiocyanato group, isothiocyanato group, formyl group, oxo group, thioformyl group, thioxo group, mercapto group, amino group, imino group, hydrazino group, aryloxy group, sulfide group, halogen group, nitro group, and silyl group.

According to a thirteenth aspect of the present invention, there is provided an electro luminescent element with the structure of the seventh aspect, wherein the derivative has a structure represented by the following formulae, (a1) to (a11) and a(13). Alternatively, the derivative may have the following norbornane structure, (a12).

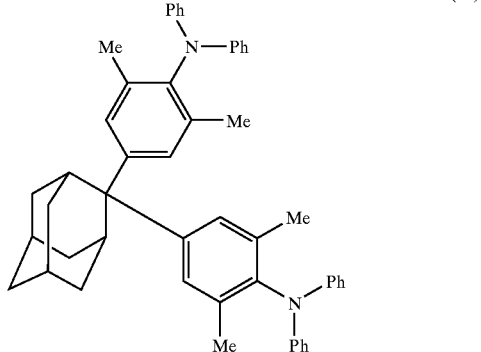

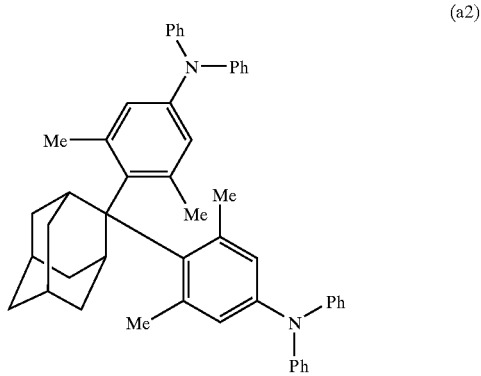

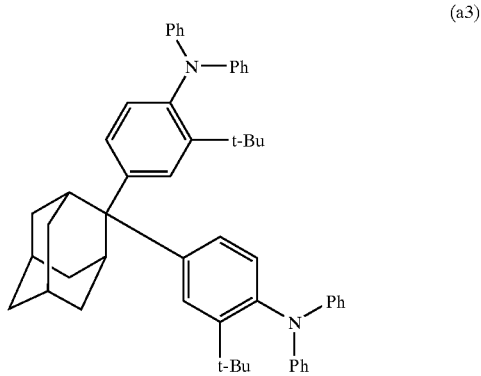

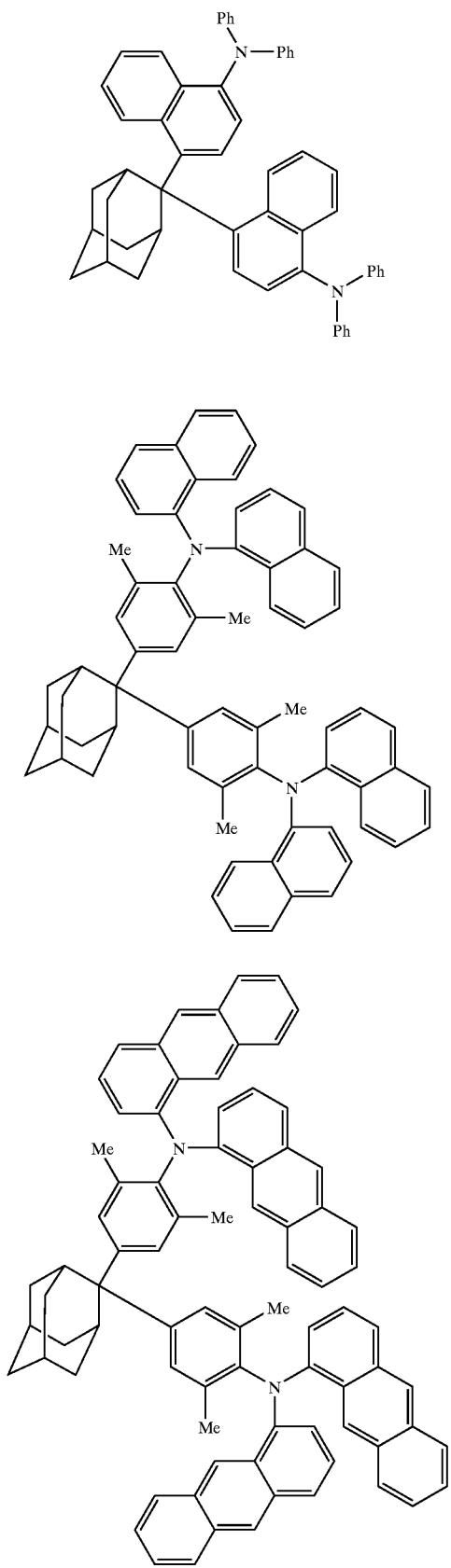
(a4)
(a5)
(a6)
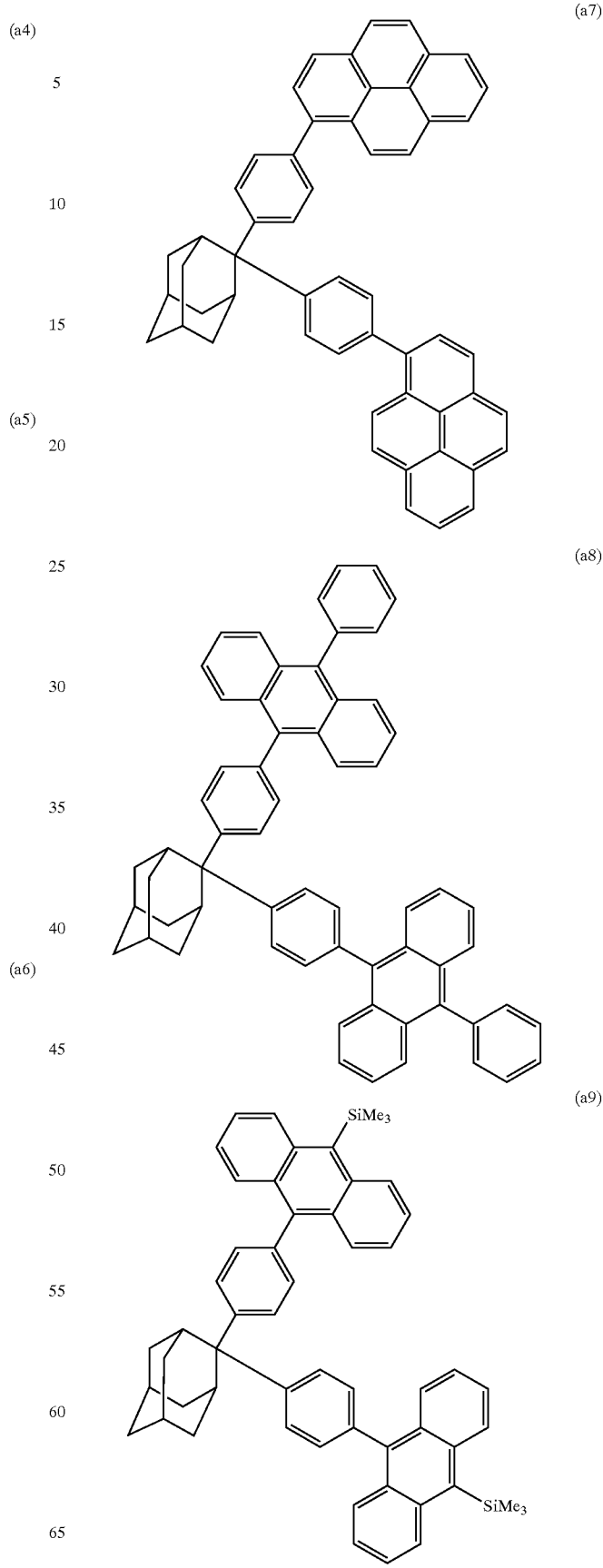
(a7)
(a8)
(a9)

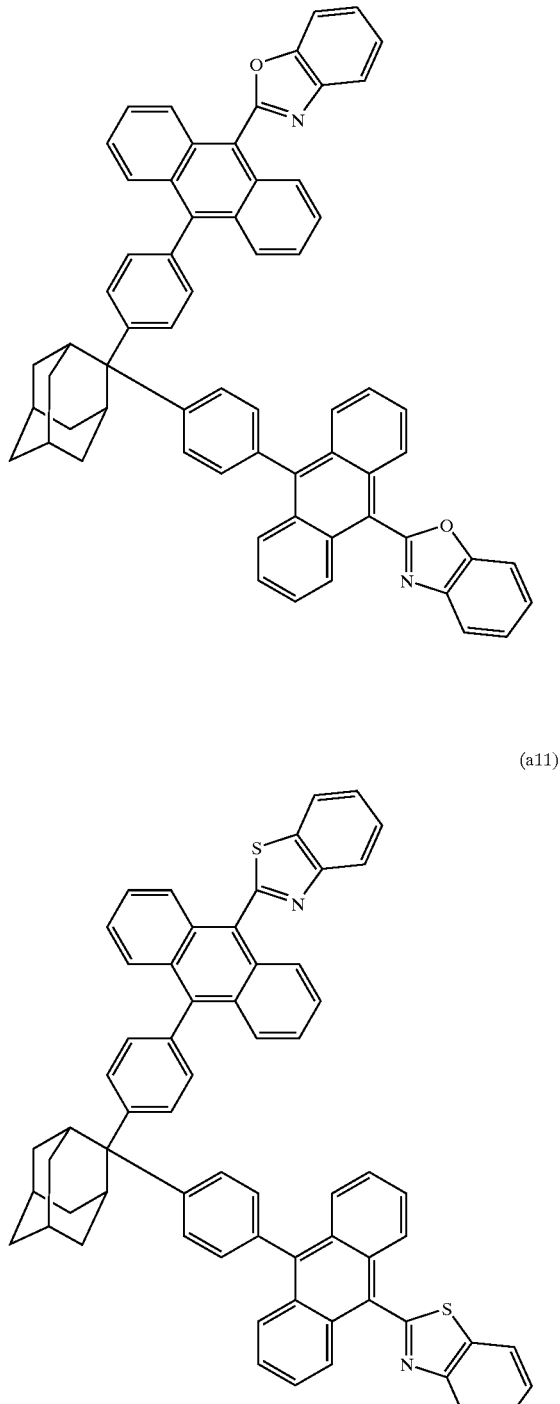
(a10)
(a11)
(a12)
(a13)
BRIEF DESCRIPTION OF THE DRAWING
FIG. 1 is a cross sectional diagram schematically showing a structure of an electro luminescent element according to the present invention.

DESCRIPTION OF THE PREFERRED EMBODIMENTS

Preferred embodiments of the present invention (hereinafter referred to as embodiments) are described hereinafter referring to the accompanying diagram.

Embodiment 1

FIG. 1 is a cross sectional diagram schematically showing a structure of an electro luminescent element according to a first embodiment of the present invention. In FIG. 1, the electro luminescent element is constructed by sequentially layering a first electrode 12 which is an anode on a transparent substrate 10, an organic compound layer 14 which emits light when electric field is applied, and a second electrode 16 which is a cathode.

The material for constructing the transparent substrate 10 includes, but not limited to, a glass substrate, a transparent ceramics substrate, and a diamond substrate. As the first electrode 12, a transparent electrode having high light permeability and conductivity is used. For example, a thin film material such as ITO (indium tin oxide), $SnO_2$, $InO_3$, and polyaniline can be used. As the second electrode 16, a metal having a low ionization potential such as Li, B, Be, Na, Mg, Al, K, Ca, and Ag, or an alloy including these metals such as MgAg, LiAl, and LiF/Al can be used.

The organic compound layer 14 provided between the first electrode 12 and the second electrode 16 is a thin film with an uniform thickness (few tens to few thousands of nm), constructed mainly from an organic compound. The organic compound layer 14 has a structure including a condensed ring compound derivative layer or a structure in which the condensed ring compound is distributed among materials which act as hosts and the host materials are further layered in the organic compound layer 14. The material acting as a host includes, for example, TPD represented by a chemical formula (1) and Alq3 represented by a chemical formula (2).

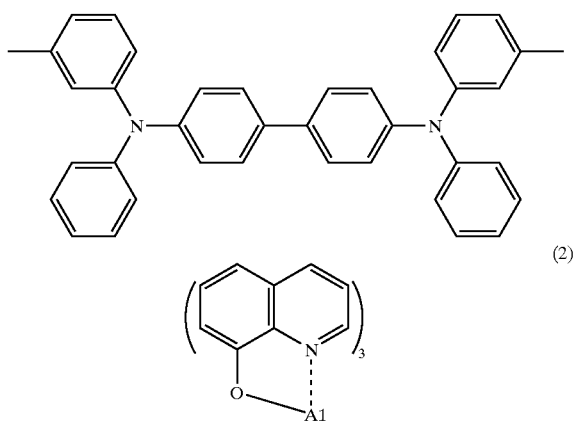

The condensed ring compound derivative mentioned here is a compound represented by a general chemical formula (3).

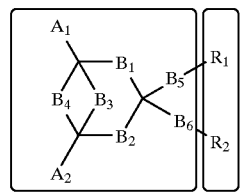

In these formula, A1 and A2 represent substituents. The substituents can be substituted by a functional group including alkyl group, aryl group, allyl group, alkene group, alkyne group, alkoxy group, hydroxyl group, hydroxylate group, thiocarboxy group, dithiocarboxy group, sulfo group, sulfino group, sulfeno group, oxycarbonyl group, haloformyl group, carbamoyl group, hydrazinocarbonyl group, amidino group, cyano group, isocyano group, cyanato group, isocyanato group, thiocyanato group, isothiocyanato group, formyl group, oxo group, thioformyl group, thioxo group, mercapto group, amino group, imino group, hydrazino group, aryloxy group, sulfide group, halogen group, nitro group, and silyl group.

B1 through B6 represent directly combined or bi functional substituents and are substituents constructed from constructing elements including alkyl group, aryl group, allyl group, alkene group, alkyne group, alkoxy group, hydroxyl group, hydroxylate group, thiocarboxy group, dithiocarboxy group, sulfo group, sulfino group, sulfeno group, oxycarbonyl group, haloformyl group, carbamoyl group, hydrazinocarbonyl group, amidino group, cyano group, isocyano group, cyanato group, isocyanato group, thiocyanato group, isothiocyanato group, formyl group, oxo group, thioformyl group, thioxo group, mercapto group, amino group, imino group, hydrazino group, aryloxy group, sulfide group, halogen group, nitro group, and silyl group.

R1 and R2 represent functional units having each of the functions of hole transporting, luminescence, and electron transporting. The example of functional units include, triphenylamine as a functional unit having hole transporting ability and represented by a chemical formula (4), coumarin as a functional, unit having luminescence and represented by a chemical formula (5), and oxadiazole derivative as a functional unit having electron transporting ability and represented by a chemical formula (6), but any functional unit can be used having hole transporting, luminescence, and/or electron transporting functions.

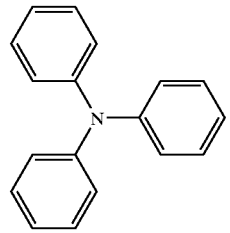

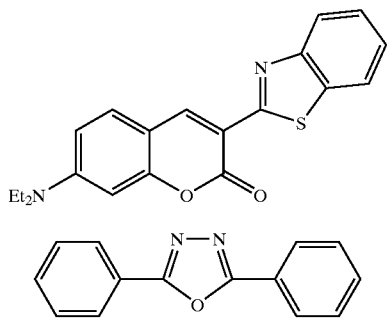

(5)

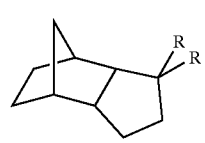

(6)

B1 through B4, R1, R2, A1, and A2 can be directly connected or connected by an aromatic ring or chain compound which is interconnected, and the connecting section can include any of the functional groups.

Examples of such a condensed ring compound derivative include compounds represented by the following chemical formulae (a) through (l). In these formulae, the functional units R1 and R2 are both represented by "R".

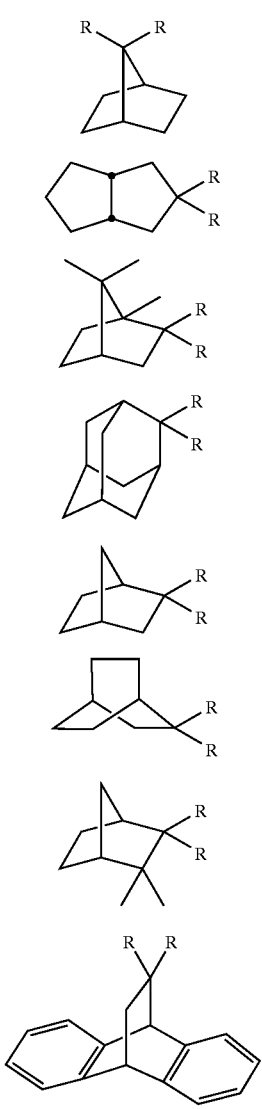

(a)

(b)

(c)

(d)

(e)

(f)

(g)

(h)

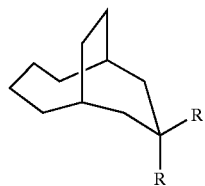

(i)

(j)

(k)

(l)

Examples of the functional units R1 and R2 include the compounds represented by the following chemical formulae (r1) through (r9).

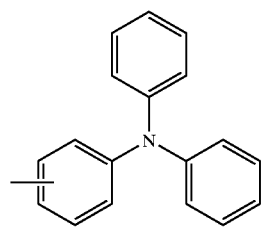

(r1)

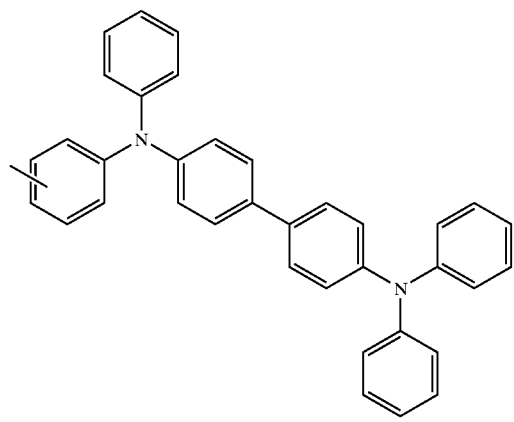

(r2)

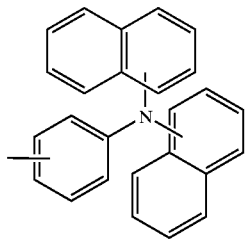
(r3)
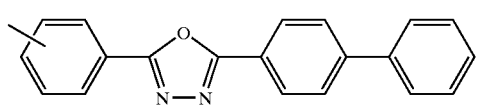
(r4)
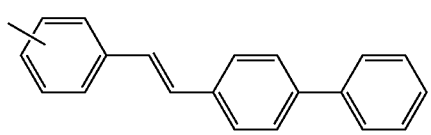
(r5)
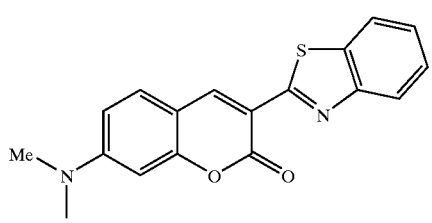
(r6)
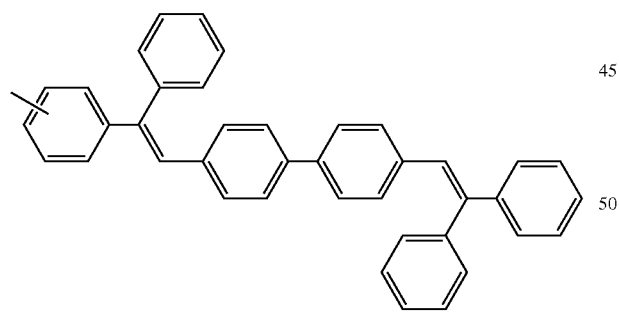
(r7)
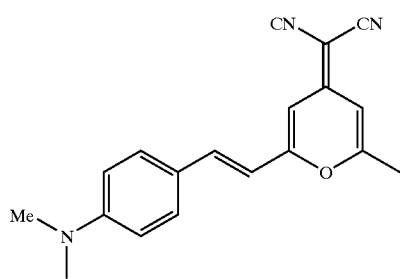
(r8)
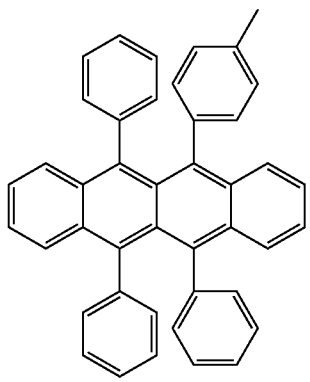
(r9)
Examples of functional units R1 and R2 can further include the compounds represented by the following chemical formulae (r10) through (r22).
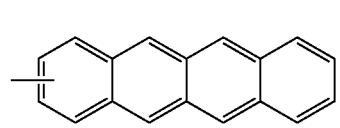
(r10)
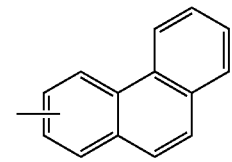
(r11)
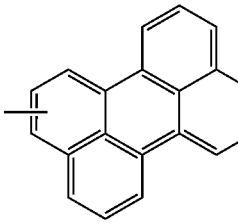
(r12)
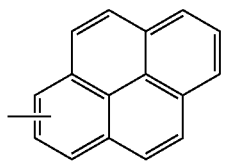
(r13)
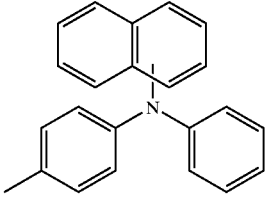
(r14)
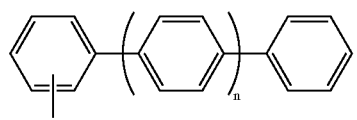
(r15)

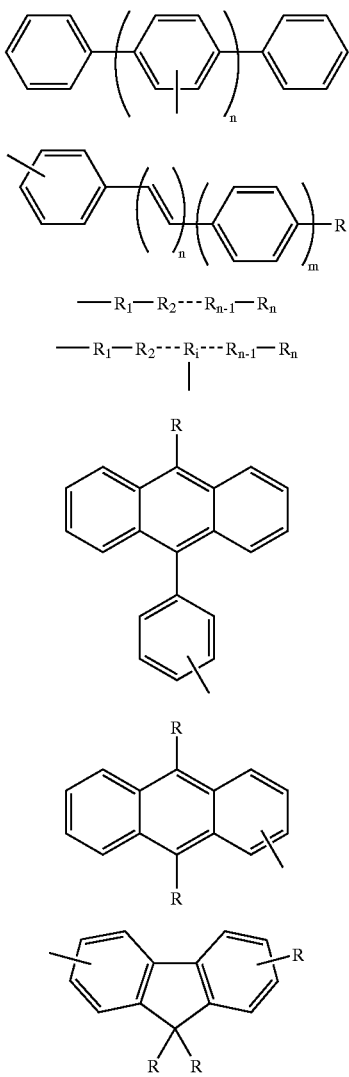

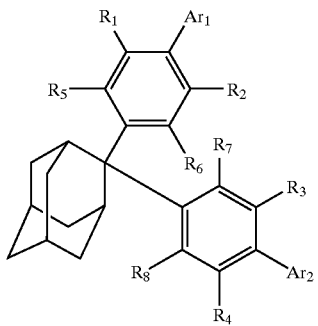

in which n, m, and l represent integers, R represents saturated hydrocarbon from C1 through C30, an isomer thereof, or an aromatic compound, such as phenyl, naphthyl, indenyl, fluorenyl, phenanthryl, anthranyl, pyrenyl, chrysenyl, naphthacenyl, benzophenanthrenyl, furanyl, thiophenyl, pyrrolyl, oxazolyl, isoxazolyl, pyrazolyl, triazolyl, furazanyl, pyridyl, oxazyl, morpholyl, thiazyl, pyridazyl, pyrimidyl, pyrazyl, triazyl, benzofuryl, isobenzofuryl, benzothiophenyl, indolyl, isoindolyl, benzoxazolyl, benzothiazolyl, benzoimidazolyl, chromenyl, quinolyl, isoquinolyl, cinnolyl, phthalazyl, quinazolyl, quinoxalyl, dibenzofuril, carbazolyl, xanthenyl, acridinyl, phenanthridinyl, phenanthryl, phenazinyl, phenoxazinyl, thianthrenyl, indolizinyl, quinolizinyl, naphthyridinyl, purinyl, oxadiazolyl, and oxathiazolyl.

The functional molecules having hole transporting ability, luminescence, and electron transporting ability, have a high crystallinity due to its general planar shape and good symmetry, and easily transform from a substable non-crystalline condition to crystallized condition by heat. By using condensed ring compound derivative as these compounds, the molecule can have a non-planar structure and reduced molecular symmetry. In this manner, the crystallinity of the molecule can be reduced. On the other hand by using a condensed ring compound, a rigid molecule skeleton of the condensed ring compound can be introduced to reduce the movability of the molecule, resulting in improvements in heat endurance.

In this manner, by using condensed ring compound derivatives for functional molecules having each of the functions of the hole transporting, luminescence, and electron transporting, low crystallinity and high heat endurance, both of which are preferable characteristics as materials for an organic electro luminescent element, can be added while maintaining superior electric characteristics.

Embodiment 2

The second preferred embodiment of the present invention has a structure such that either an adamantane derivative layer is included in the organic compound layer 14 of the electro luminescent element shown in FIG. 1 or the adamantane derivative is distributed among materials that act as hosts with the hosts further layered in the organic compound layer 14. Examples of the material that acts as a host include TPD represented by (1) and Alq3 represented by (2).

Here, the adamantane derivative is a compound represented by the following general chemical formula (7).

Ar1 and Ar2 represent substituents and composed of compounds with hole transporting ability, luminescence, and electron transporting ability. The substituents have the basic skeleton as an aryl skeleton such as phenyl, naphthyl, and phenanthryl. The substituents can further be substituted by, for example, a functional group selected from a group of alkyl group, aryl group, allyl group, alkene group, alkyne group, alkoxy group, hydroxyl group, hydroxylate group, thiocarboxy group, dithiocarboxy group, sulfo group, sulfino group, sulfeno group, oxycarbonyl group, haloformyl group, carbamoyl group, hydrazinocarbonyl group, amidino group, cyano group, isocyano group, cyanato group, isocyanato group, thiocyanato group, isothiocyanato group, formyl group, oxo group, thioformyl group, thioxo group, mercapto group, amino group, imino group, hydrazino group, aryloxy group, sulfide group, halogen group, nitro group, and silyl group.

R1 through R8 represent substituents and can be, for example, functional groups including alkyl group, aryl group, allyl group, alkene group, alkyne group, alkoxy group, hydroxyl group, hydroxylate group, thiocarboxy group, dithiocarboxy group, sulfo group, sulfino group, sulfeno group, oxycarbonyl group, haloformyl group, carbamoyl group, hydrazinocarbonyl group, amidino group, cyano group, isocyano group, cyanato group, isocyanato group, thiocyanato group, isothiocyanato group, formyl group, oxo group, thioformyl group, thioxo group, mercapto group, amino group, imino group, hydrazino group, aryloxy group, sulfide group, halogen group, nitro group, and silyl group.

Connection between Ar1 and Ar2 and interconnection between R1 through R8 can be achieved by directly connecting or by connecting using 2 functional substituents. The connection section can include any of the functional groups mentioned above.

As described above, a compound according to the present invention has an adamantane derivative as its basic skeleton.

The adamantane skeleton has a high strength and high heat endurance, as can be seen from its ability to stably sublimate at a temperature greater than or equal to 200° C. The adamantane derivative according to the present invention has the adamantane skeleton within the molecule as a cross-linkage point. Because of this, the molecule is fixed with high strength and rigidity and with a good heat enduring ability.

By introducing substituents in R1 through R8, heat endurance and endurance improve compared to a case without the substituents. By introducing the substituents, rotations around the connecting axes between the adamantane and benzene ring and between the benzene ring and substituent molecule are constrained, resulting in decrease in the movability of the molecule and thus improvements in heat endurance. As a substitute, a substitute with a size of methyl group is sufficiently effective, as shown in the following (8) and (9), but the heat endurance improvement is more effective if a substituent with a higher mass such as t-Bu and triphenylsilyl group etc., as shown in (10) is introduced.

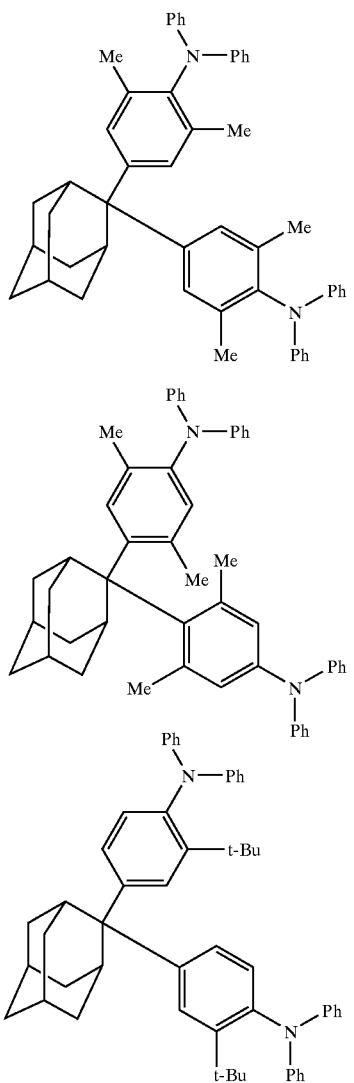

Similarly, rotation of compounds with the benzene ring section replaced by a naphthalene ring, represented by following (11), is constrained, resulting in an improvement in the heat endurance when compared to a case without substituents.

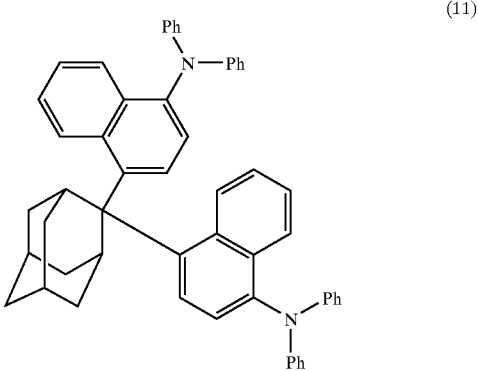

As can be seen from following (12) and (13), by increasing the degree of condensing from diphenylamine to dinaphthylamine and dianthranilamine, the ionization potential as a hole transporting material is decreased, so that holes can more easily be injected from the transparent electrode, resulting in an improvement in the luminescence of the electro luminescent element. At the same time, rotation of the molecule is constrained, thus the structure effectively improves the heat endurance.

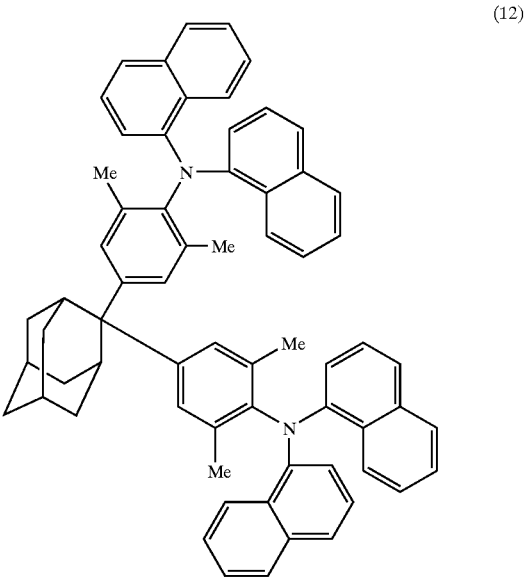

(13)

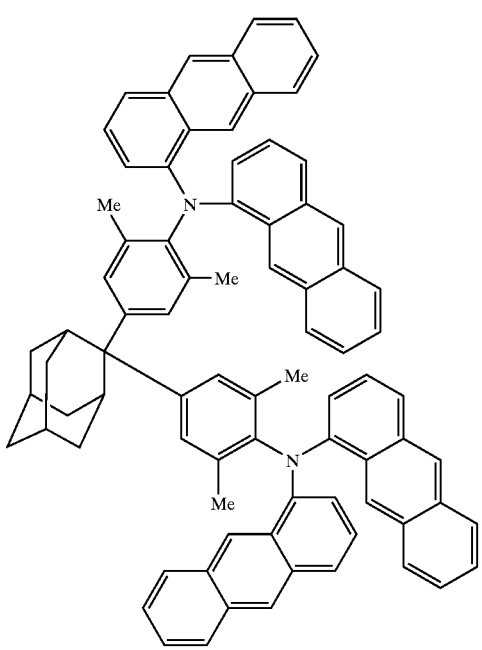

These compounds can be synthesized generally by a coupling reaction between an adamantane amine compound and aromatic halogen compound, or by a coupling reaction between an adamantane halogen compound, adamantane borate, adamantane sulfonyl ether, adamantane ether, or adamantane ester and aromatic amine compound, but the obtaining method is not limited to these.

EXPERIMENT

Comparative experimental examples are described below, where an adamantane derivative was synthesized, an electro luminescent element was produced using the adamantane derivative, and the performance was examined.

Example 1

Synthesis of Dianilinoadamantane (14)

A mixture of 13 g of 2-adamantanone, 55 g of aniline, and 15 g of aniline hydrochloride was introduced to a flask with a water remover. The mixture was heated and refluxed at 200° C. (oil bath) under nitrogen atmosphere. Forty hours later, a KOH solution was added so that the pH was approximately 10, and the mixture was extracted with chloroform and washed with water. The mixture was then dried with sodium sulfate, evaporated, and purified with silica gel column chromatography, to obtain 5 g of dianilinoadamantane as a colorless amorphous material.

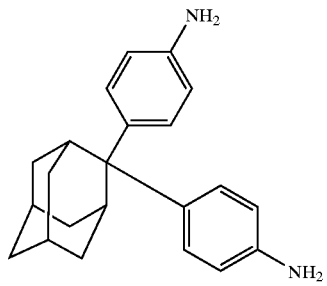

(14)

Example 2

Synthesis of Ditoluidinoadamantane (15)

A mixture of 13 g of 2-adamantanone, 60 g of o-toluidine, and 18 g of o-toluidine hydrochloride was introduced to a flask with a water remover. The mixture was heated and refluxed at 250° C. (oil bath) under nitrogen atmosphere. Sixty hours later, a KOH solution was added so that the pH was approximately 10, and the mixture was extracted with chloroform and washed with water. The mixture was then dried with sodium sulfate, evaporated, and purified with silica gel column chromatography, to obtain 4.2 g of ditoluidinoadamantane as a white solid.

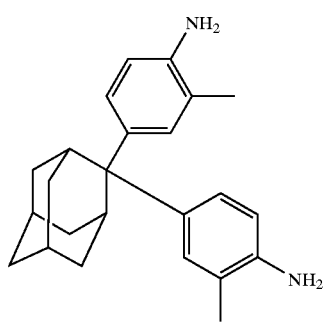

(15)

Example 3

Synthesis of Didimethylanilinoadamantane (16)

A mixture of 13 g of 2-adamantanone, 63 g of 2,6-dimethylaniline, and 20 g of 2,6-dimethylaniline hydrochloride was introduced to a flask with a water remover. The mixture was heated and refluxed at 250° C. (oil bath) under nitrogen atmosphere. Eighty hours later, a KOH solution was added so that the pH was approximately 10, and the mixture was extracted with chloroform and washed with water. The mixture was then dried with sodium sulfate, evaporated, and purified with silica gel column chromatography, to obtain 6.5 g of didimethylanilinoadamantane as a white solid.

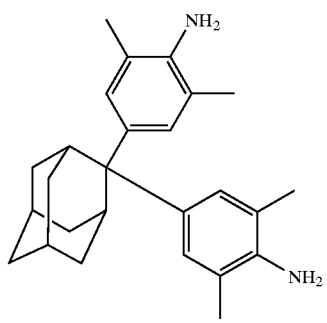

(16)

Example 4

Synthesis of a Hole Transporting Molecule (17)

A mixture of 252 mg of dianilinoadamantane (compound 14), 1.0 g of iodobenzene, 1.1 g of potassium carbonate, 700 mg of copper powder, 250 mg of CuO, and 5 g of decalin was heated and stirred for 31 hours under nitrogen atmosphere at 170° C. The mixture was then purified by silica gel column chromatography (chloroform-hexane 1:1) to obtain 115 mg of a hole transporting molecule (17).

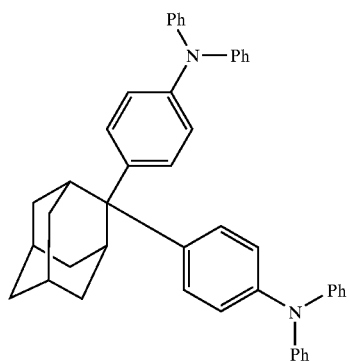

(17)

Example 5

Synthesis of a Hole Transporting Molecule (18)

A mixture of 253 mg of dianilinoadamantane (compound 14), 1.0 g of 1-iodonaphthalene, 1.1 g of potassium carbonate, 700 mg of copper powder, 270 mg of CuO, and 3.5 g of decalin was heated and stirred under nitrogen atmosphere for 30 hours at 170° C. The mixture was then purified by silica gel column chromatography (chloroform-hexane 1:1) to obtain 133 mg of a hole transporting molecule (18).

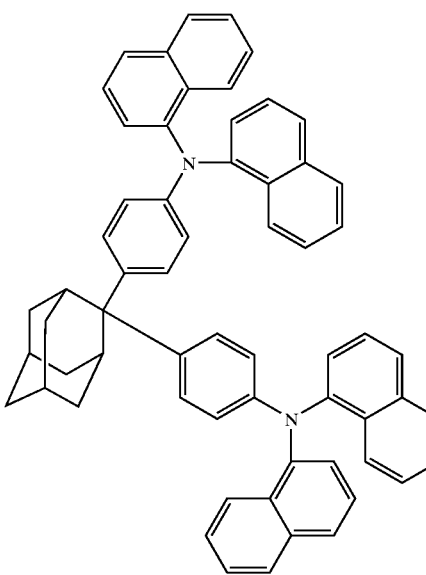

(18)

Example 6

Synthesis of a Hole Transporting Molecule (19)

A mixture of 250 mg of ditoluidinoadamantane (15), mentioned above, 1.0 g of iodobenzene, 1.1 g of potassium carbonate, 700 mg of copper powder, 250 mg of CuO, and 5 g of decalin was heated and stirred under nitrogen atmosphere for 35 hours at 170° C. The mixture was then purified by silica gel column chromatography (chloroform-hexane 1:1) to obtain 95 mg of hole transporting molecule (19).

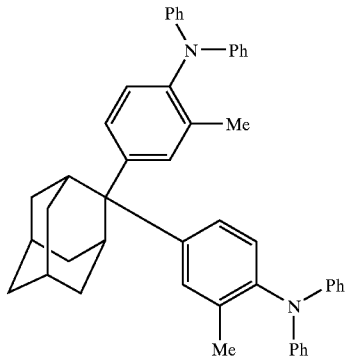

(19)

Example 7

Synthesis of a Hole Transporting Molecule (8)

A mixture of 252 mg of didimethylanilinoadamantane (16), mentioned above, 1.0 g of iodobenzene, 1.1 g of potassium carbonate, 700 mg of copper powder. 250 mg of CuO, and 5 g of decalin was heated and stirred under nitrogen atmosphere for 30 hours at 170° C. The mixture was then purified by silica gel column chromatography (chloroform-hexane 1:1) to obtain 75 mg of hole transporting molecule (8).

Example 8

Glass Transition Temperatures of the Hole Transporting Molecules

Glass transition temperatures of the hole transporting molecules (17), (18), (19), and (8) measured by differential scanning calorimeter (DSC) were respectively 110° C., 135° C., 150° C., and 165° C.

Comparative Example 1

Glass Transition Temperature of a Hole Transporting Molecule

The glass transition temperature of TPD measured by differential scanning calorimeter (DSC) was 65° C.

Example 9

An electro luminescent element was prepared as follows using the hole transporting molecule (17) mentioned above. An ITO electrode was formed on a glass substrate and the hole transporting molecule (17) was vacuum evaporated with a thickness of 60 nm as a hole transporting layer. 60 nm of $Alq_3$, which is the electron transporting molecule was co-evaporated on top of this layer. Finally, a Mg/Ag electrode (9:1) was evaporated to produce an electro luminescent element. The element was driven under nitrogen gas atmosphere at room temperature. When an electric current of 10 mA/cm$^2$ was injected, green color luminescence having a luminance of 150 cd/m$^2$ was obtained with a half life of luminance of 1000 hours.

Example 10

An electro luminescent element was prepared as follows using the hole transporting molecule (17) defined above. An ITO electrode was formed on a glass substrate and the hole transporting molecule (17) was vacuum evaporated with a thickness of 60 nm as a hole transporting layer. 60 nm of $Alq_3$ as the electron transporting molecule was co-evaporated on top of this layer. Finally, a Mg/Ag electrode (9:1) was evaporated to produce an electro luminescent element. The element was driven in a nitrogen gas atmosphere at room temperature. When an electric current of 10 mA/m$^2$ was injected, green color luminescence having a luminance of 150 cd/m$^2$ was obtained with the half life of luminance being 1000 hours. Temperature was raised while driving the element at 10 mA/cm$^2$. The element breakdown occurred at 110° C.

Example 11

An electro luminescent element was prepared as follows using the hole transporting molecule (18) mentioned above. An ITO electrode was formed on a glass substrate and the hole transporting molecule (18) was vacuum evaporated with a thickness of 60 nm as a hole transporting layer. 60 nm of $Alq_3$ as the electron transporting molecule was co-evaporated on top of this layer. Finally, a Mg/Ag electrode (9:1) was evaporated to produce an electro luminescent element. The element was driven in a nitrogen gas atmosphere at room temperature. When an electric current of 10 mA/cm$^2$ was injected, green color luminescence having a luminance of 200 cd/m$^2$ was obtained with a half life of luminance of 1500 hours. Temperature was raised while driving the element at 10 mA/cm$^2$. The element breakdown occurred at 135° C.

Example 12

An electro luminescent element was prepared as follows using the hole transporting molecule (19) defined above. An ITO electrode was formed on a glass substrate and the hole transporting molecule (19) was vacuum evaporated with a thickness of 60 nm as a hole transporting layer. 60 nm of $Alq_3$ as the electron transporting molecule was co-evaporated on top of this layer. Finally, a Mg/Ag electrode (9:1) was evaporated to produce an electro luminescent element. The element was driven in a nitrogen gas atmosphere at room temperature. When an electric current of 10 mA/cm$^2$ was injected, green color luminescence having a luminance of 200 cd/m$^2$ was obtained with a half life of luminance of 1800 hours. Temperature was raised while driving the element at 10 mA/cm$^2$. The element breakdown occurred at 150° C.

Example 13

An electro luminescent element was prepared as follows using the hole transporting molecule (8) defined above. An ITO electrode was formed on a glass substrate and the hole transporting molecule (8) was vacuum evaporated with a thickness of 60 nm as a hole transporting layer. 60 nm of $Alq_3$ as the electron transporting molecule was co-evaporated on top of this layer. Finally, a Mg/Ag electrode (9:1) was evaporated to produce an electro luminescent element. The element was driven in a nitrogen gas atmosphere at room temperature. When an electric current of 10 mA/cm$^2$ was injected, green color luminescence having a luminance of 190 cd/m$^2$ was obtained with a half life of luminance of 2200 hours. Temperature was raised while driving the element at 10 mA/cm$^2$. The element breakdown occurred at 165° C.

Example 14

20 g of dianilinoadamantane (compound 14) was dissolved in a mixture of 50 ml of sulfuric acid and 20 ml of acetic acid. 5 g of sodium nitrite was added to the solution under ice cooling and stirring. 15 minutes later, 15 g of potassium iodide was added. After stirring the solution for 30 minutes under room temperature and reacting for one hour at 80° C., 500 ml of water was added, and the solution was filtered and washed with water. After recrystallizing with toluene, 12 g of diiodophenyladamanatane (compound 20) was obtained.

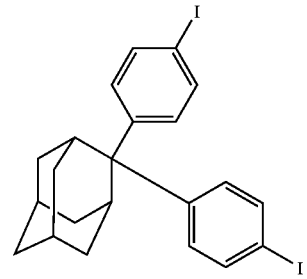

(20)

Example 15

300 mg of diiodophenyladamantane (compound 20), 510 mg of pyrenyl borate, 20 mg of Pd(PPh$_3$)$_4$, 400 mg of triethylamine, and 3 g of DMF were mixed, degassed, and then stirred and heated for 5 hours at 100° C. After DMF was removed, the mixture was separated with water-chloroform, dried with sodium sulfate, and evaporated. The mixture was purified by column chromatography (silica-chloroform:hexane=1:2) to obtain 150 mg of dipyrenylphenyladamantane (compound 21). The mixture was purified by column chromatography (silica-chloroform:hexane=1:2) to obtain 150 mg of dipyrenyladamantane (compound 21).

An organic electro luminescent element using the compound 21 was prepared in the following steps. An ITO electrode was formed on a glass substrate and 60 nm of NPD (N,N'-dinaphthyl-N,N'-phenylbenzidine) was vacuum evaporated on the ITO layer as a hole transporting layer. 40 nm of compound 21 was evaporated on this layer as a luminescence layer and 20 nm of Alq3 (compound 2) was evaporated as an electron transporting layer. Finally, a Mg/Ag electrode (9:1) was evaporated to produce an organic electro luminescent element. The element was driven in a nitrogen gas atmosphere at room temperature. When an electric current of 10 mA/cm² was injected, a blue luminescence with a luminance of 250 cd/m² was obtained, and the half life of the luminance was 1000 hours.

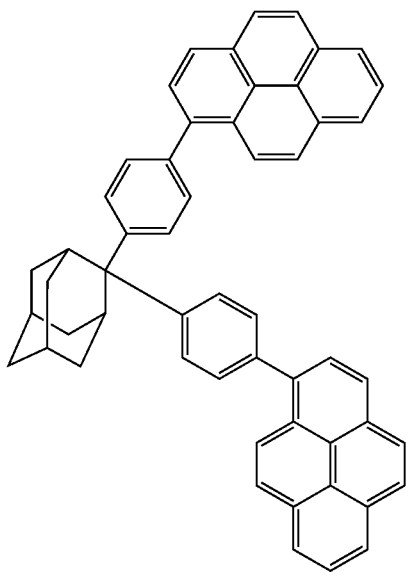

(21)

Example 16

250 mg of diiodophenyladamantane (compound 20), 510 mg of 10-(9-phenylanthryl) borate, 20 mg of Pd(PPh₃)₄, 350 mg of triethylamine, and 2.5 g of DMF were mixed, degassed, and then stirred and heated for 15 hours at 100° C. After DMF was removed, the mixture was separated with water-chloroform, dried with sodium sulfate, and evaporated. The mixture was purified by column chromatography (silica-chloroform:hexane=1:3) to obtain 100 mg of di(9-phenylanthrylphenyl)adamantane (compound 22).

An organic electro luminescent element using the compound 22 was prepared in the following steps. An ITO electrode was formed on a glass substrate and 60 nm of NPD was vacuum evaporated on the ITO layer as a hole transporting layer. 40 nm of compound 22 was evaporated on this layer as a luminescence layer and 20 nm of Alq3 (compound 2) was evaporated as an electron transporting layer. Finally, a Mg/Ag electrode (9:1) was evaporated to produce an organic electro luminescent element. The element was driven in a nitrogen gas atmosphere at room temperature. When an electric current of 10 mA/cm² was injected, a blue luminescence with a luminance of 180 cd/ml was obtained, and the half life of the luminance was 1700 hours.

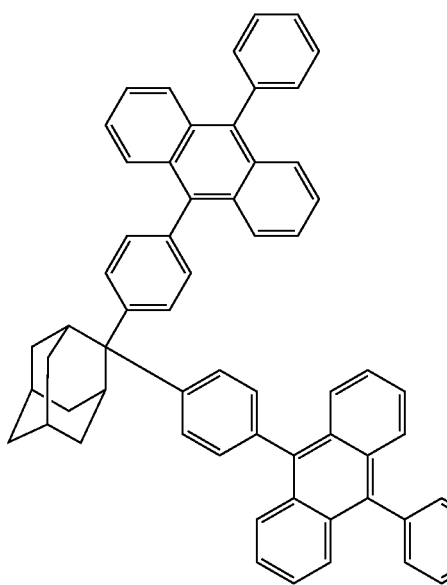

(22)

Example 17

100 mg of diiodophenyladamantane (compound 20), 650 mg of 10-(9-trimethylsilylanthryl) borate, 20 mg of Pd(PPh₃)₄, 250 ml of triethylamine, and 3 g of DMF were mixed, degassed, and then stirred and heated for 20 hours at 100° C. After DMF was removed, the mixture was separated with water-chloroform, dried with sodium sulfate, and evaporated. The mixture was purified by column chromatography (silica-chloroform:hexane=1:5) to obtain 75 mg of di(9-trimethylsilylanthrylphenyl)adamantane (compound 23).

An organic electro luminescent element using compound 23 was prepared in the following steps. An ITO electrode was formed on a glass substrate and 60 nm of NPD was vacuum evaporated on the ITO layer as a hole transporting layer. 40 nm of compound 23 was evaporated on this layer as a luminescence layer and 20 nm of Alq3 (compound 2) was evaporated as an electron transporting layer. Finally, a Mg/Ag electrode (9:1) was evaporated to produce an organic electro luminescent element. The element was driven in a nitrogen gas atmosphere at room temperature. When an electric current of 10 mA/cm² was injected, a blue luminescence with a luminance of 220 cd/m² was obtained, and the half life of the luminance was 800 hours.

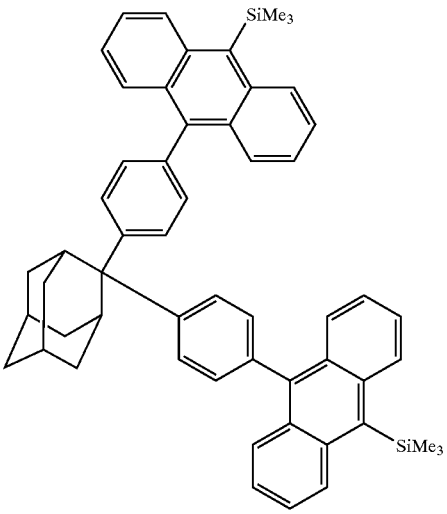

(23)

Example 18

150 mg of diiodophenyladamantane (compound 20), 700 mg of 10-(9-benzoxazolylanthryl) borate, 20 mg of Pd(PPh$_3$)$_4$, 350 mg of triethylamine, and 3 g of DMF were mixed, degassed, and then stirred and heated for 15 hours at 100° C. After DMF was removed, the mixture was separated with water-chloroform, dried with sodium sulfate, and evaporated. The mixture was purified by column chromatography (silica-chloroform:hexane=1:3) to obtain 85 mg of adamantane di(9-benzoxazolylanthrylphenyl) adamantane (compound 24).

An organic electro luminescent element using compound 24 was prepared in the following steps. An ITO electrode was formed on a glass substrate and 60 nm of NPD was vacuum evaporated on the ITO layer as a hole transporting layer. 40 nm of compound 24 was evaporated on this layer as a luminescence layer and 20 nm of Alq3 (compound 2) was evaporated as an electron transporting layer. Finally, a Mg/Ag electrode (9:1) was evaporated to produce an organic electro luminescent element. The element was driven in a nitrogen gas atmosphere at room temperature. When an electric current of 10 mA/cm$^2$ was injected, a blue luminescence with a luminance of 250 cd/m$^2$ was obtained, and the half life of the luminance was 1200 hours.

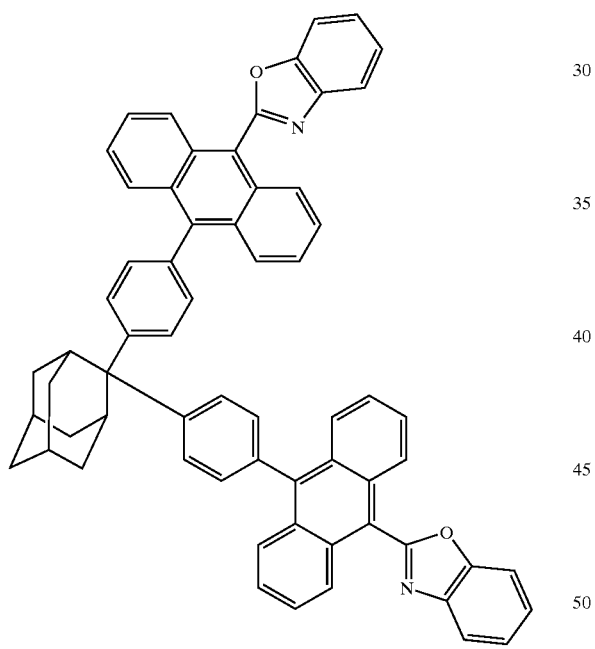

(24)

Example 19

150 mg of diiodophenyladamantane (compound 20), 700 mg of 10-(9-benzothiazolylanthryl) borate, 20 mg of Pd(PPh$_3$)$_4$, 350 mg of triethylamine, and 3 g of DMF were mixed, degassed, and then stirred and heated for 24 hours at 100° C. Ar DMF was removed, the mixture was separated with water-chloroform, dried with sodium sulfate, and evaporated. The mixture was purified by column chromatography (silica-chloroform:hexane=1:3) to obtain 85 mg of di(9-benzothiazolylanthrylphenyl)adamantane (compound 25).

An organic electro luminescent element using compound 25 was prepared in the following steps. An ITO electrode was formed on a glass substrate and 60 nm of NPD was vacuum evaporated on the ITO layer as a hole transporting layer. 40 nm of compound 25 was evaporated on this layer as a luminescence layer and 20 nm of Alq3 (compound 2) was evaporated as an electron transporting layer. Finally, a Mg/Ag electrode (9:1) was evaporated to produce an organic electro luminescent element. The element was driven in a nitrogen gas atmosphere at room temperature. When an electric current of 10 mA/cm$^2$ was injected, a blue luminescence with a luminance of 180 cd/m$^2$ was obtained, and the half life of the luminance was 2000 hours.

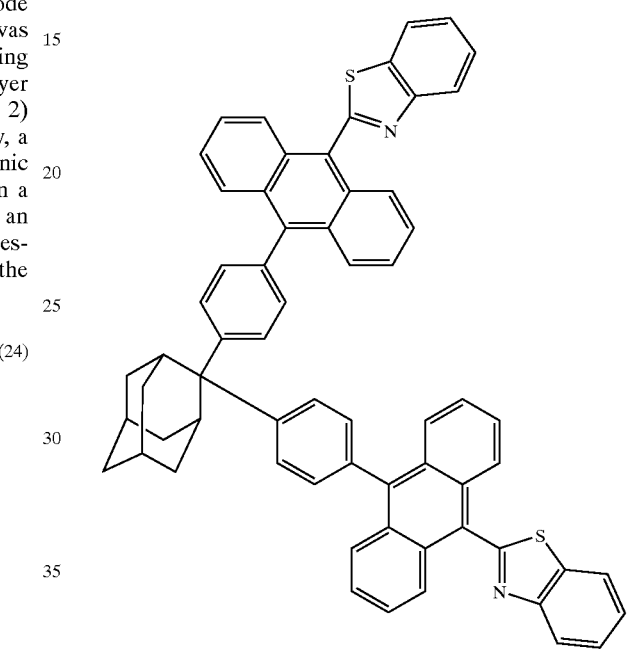

(25)

Example 20

Dianilinonorbornane was synthesized from norbornanone in a similar manner to the synthesis of dianilinoadamantane (compound 14) and diiodophenylnorbornane (compound 26) was synthesized from dianilinonorbornane in a similar manner to the Example 14.

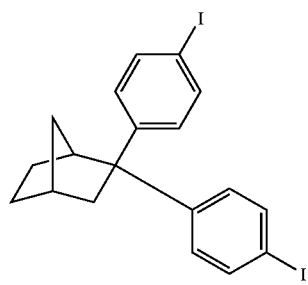

(26)

Example 21

200 mg of diiodophenylnorbornane (compound 26), 800 mg of 10-(9-benzothiazolylanthryl) borate, 20 mg of Pd(PPh$_3$)$_4$, 400 mg of triethylamine, and 3 g of DMF were mixed, degassed, and then stirred and heated for 32 hours at 100° C. After DMF was removed, the mixture was separated with water-chloroform, dried with sodium sulfate, and evaporated. The mixture was purified by column chromatography (silica-chloroform:hexane=1:5) to obtain 120 mg of di(9-benzothiazolylanthrylphenyl) norbornane (compound 27).

An organic electro luminescent element using compound 27 was prepared in the following steps. An ITO electrode was formed on a glass substrate and 60 nm of NPD was vacuum evaporated on the a ITO layer as a hole transporting layer. 40 nm of compound 27 was evaporated on this layer as a luminescence layer and 20 nm of Alq3 (compound 2) was evaporated as an electron transporting layer. Finally, a Mg/Ag electrode (9:1) was evaporated to produce an organic electro luminescent element. The element was driven in a nitrogen gas atmosphere at room temperature. When an electric current of 10 mA/cm$^2$ was injected, a blue luminescence with a luminance of 250 cd/m$^2$ was obtained, and the half life of the luminance was 1200 hours.

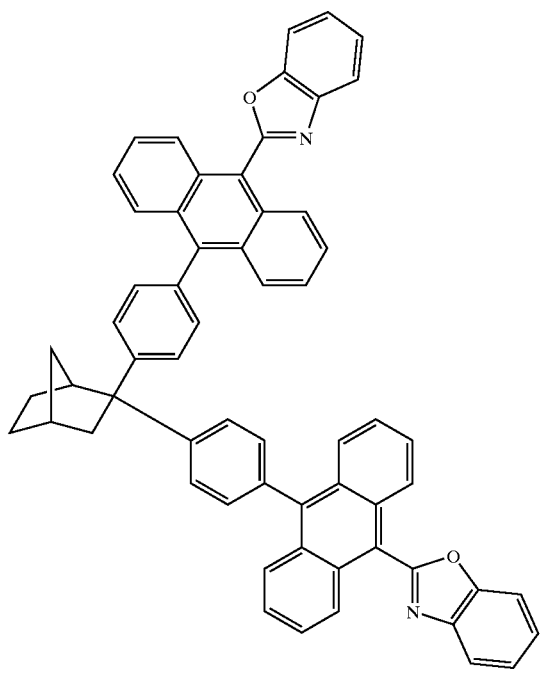

(27)

Example 22

150 mg of diiodophenyladamantane (compound 20), 800 mg of 5-phenanthryl borate, 20 mg of Pd(PPh$_3$)$_4$, 340 mg of triethylamine, and 3 g of DMP were mixed, degassed, and then stirred and heated for 25 hour at 100° C. After DMF was removed, the mixture was separated with water-chloroform, dried with sodium sulfate, and evaporated. The mixture was purified by column chromatography (silica-chloroform:hexane=1:3) to obtain 85 mg of diphenanthrylphenyladamantane (compound 28).

An organic electro luminescent element using compound 28 was prepared in the following steps. An ITO electrode was formed on a glass substrate and 60 nm of NPD was vacuum evaporated on the ITO layer as a hole transporting layer. 40 nm of compound 24 was evaporated on this layer as a luminescence layer and 20 nm of compound 28 was evaporated as an electron transporting layer. Finally, a Mg/Ag electrode (9:1) was evaporated to produce an organic electro luminescent element. The element was driven in a nitrogen gas atmosphere at room temperature. When an electric current of 10 mA/cm$^2$ was injected, a blue luminescence with a luminance of 330 cd/m$^2$ was obtained, and the half life of the luminance was 1800 hours.

As described, according to the present invention, by using a condensed ring compound derivative or an adamantane derivative as the hole transporting, luminescence, and electron transporting molecule, low crystallinity and high heat endurance, which are preferable characteristics as a material for an organic electro luminescent element, can be imparted to the element while maintaining superior electric characteristics.

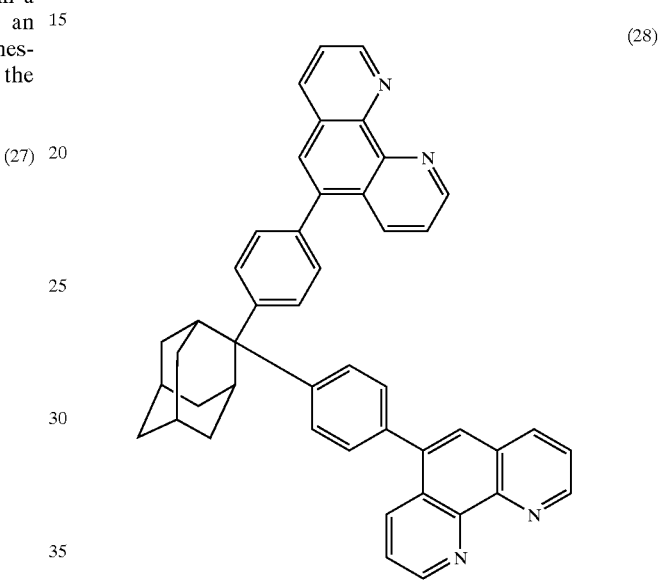

(28)

What is claimed is:
1. An electro luminescent element comprising at least one organic compound layer between electrodes wherein at least one said organic compound layer comprises a condensed ring compound derivative represented by one of the following chemical formulae, (a) to (1):

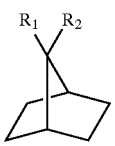

(a)

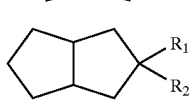

(b)

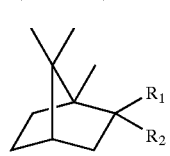

(c)

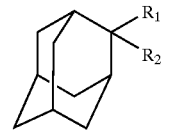

(d)

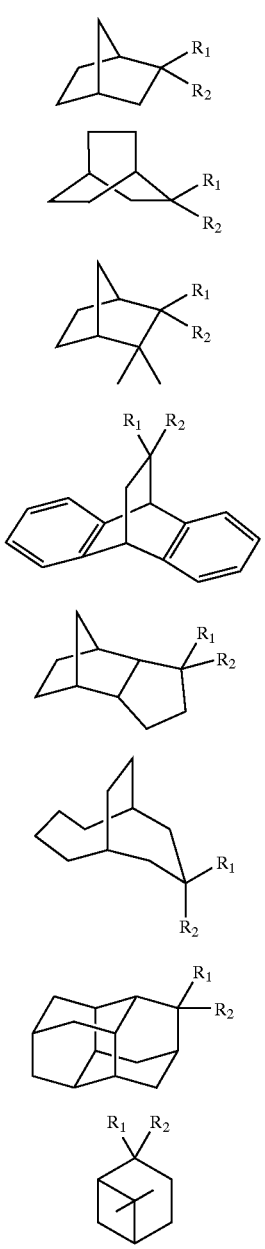
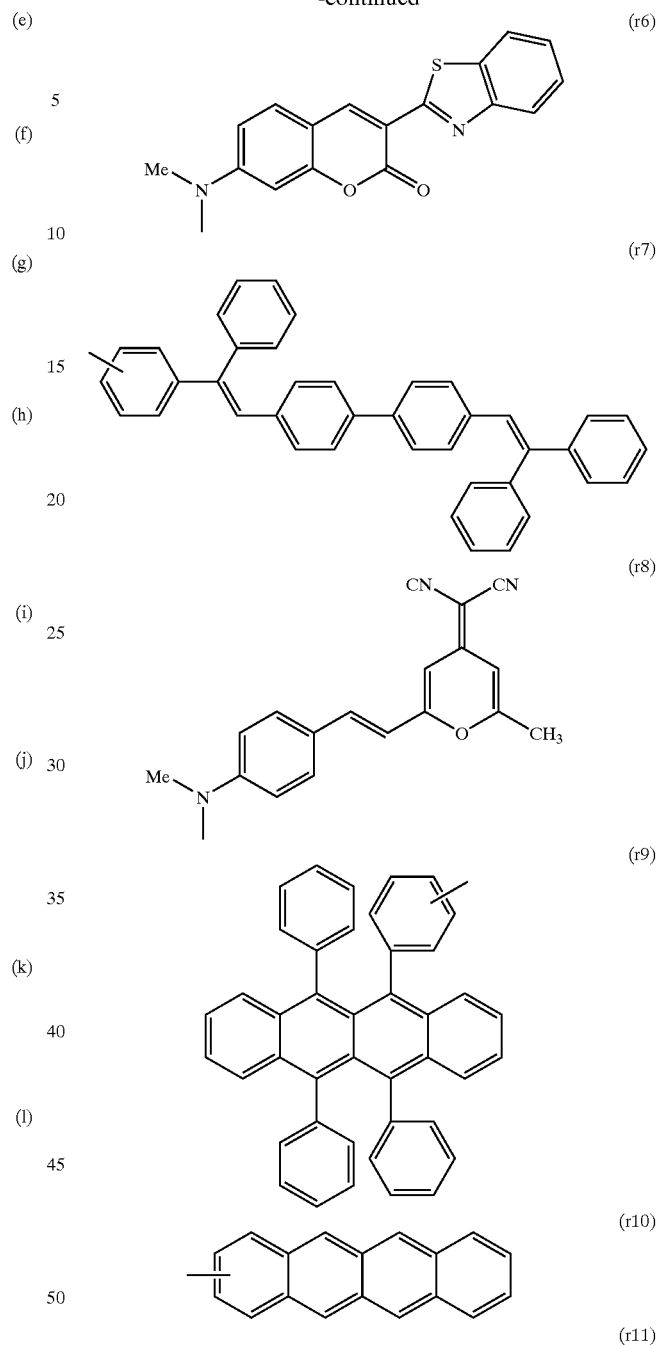
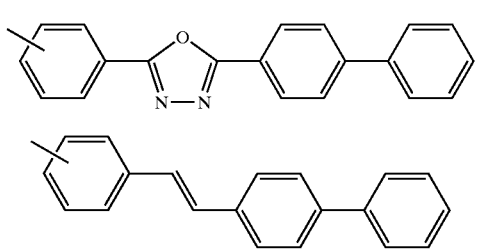
wherein R₁ and R₂ individually and independently represents a functional unit represented by one of the chemical formulae, (r4) to (r17) or (r20) to (r22):
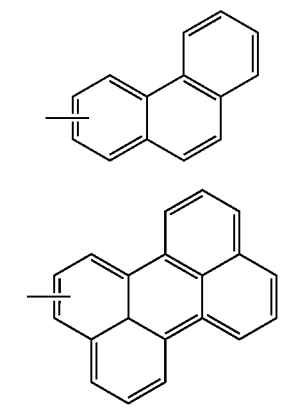

-continued (r13) 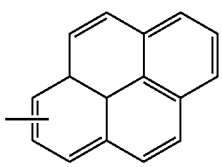

(r14) 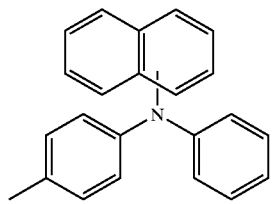

(r15) 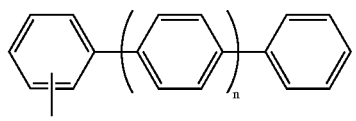

(r16) 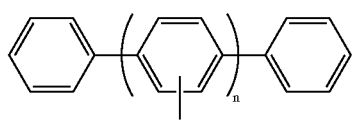

(r17) 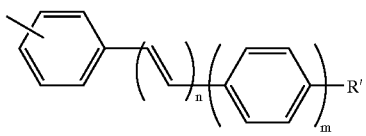

(r20) 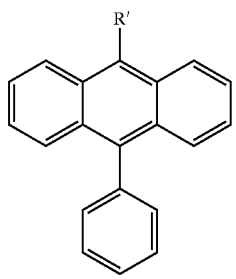

(r21) 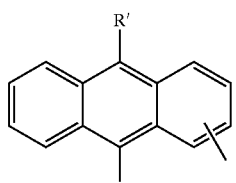

(r22) 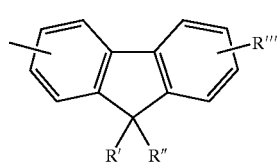

wherein n and m represent positive integers, and R', R" and R'" individually and independently represent saturated hydrocarbon from $C_1$ through $C_{30}$ or an aromatic group.

2. An electro luminescent element according to claim 1, wherein R', R" and R'" individually and independently are selected from the group consisting of phenyl, naphthyl, indenyl, fluorenyl, phenanthryl, anthranyl, pyrenyl, chrysenyl, naphthacenyl, benzophenanthrenyl, furanyl, thiophenyl, pyrrolyl, oxazolyl, isoxazolyl, pyrazolyl, triazolyl, furazanyl, pyridyl, oxazyl, morpholyl, thiazyl, pyridazyl, pyrimidyl, pyrazyl, triazyl, benzofuryl, isobenzofuryl, benzothiophenyl, indolyl, isoindolyl, benzoxazolyl, benzothiazolyl, benzoimidazolyl, chromenyl, quinolyl, isoquinolyl, cinnolyl, phthalazyl, quinazolyl, quinoxalyl, dibenzofuril, carbazolyl, xanthenyl, acridinyl, phenanthridinyl, phenanthryl, phenazinyl, phenoxazinyl, thianthrenyl, indolizinyl, quinolizinyl, naphthyridinyl, purinyl, oxadiazolyl, oxathiazolyl and combinations thereof.

3. An electro luminescent element comprising at least one organic compound layer between electrodes, wherein, at least one said organic compound layer comprises an adamantane derivative represented by one of the following chemical formulae (a4) to (a11) or (a13):

(a4)
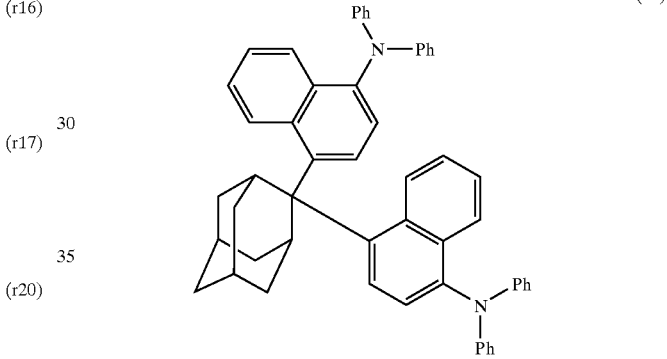

(a5)
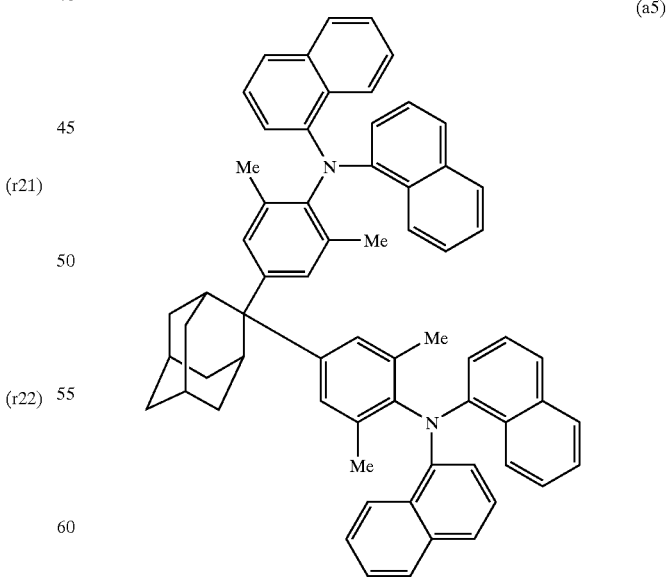

(a6)
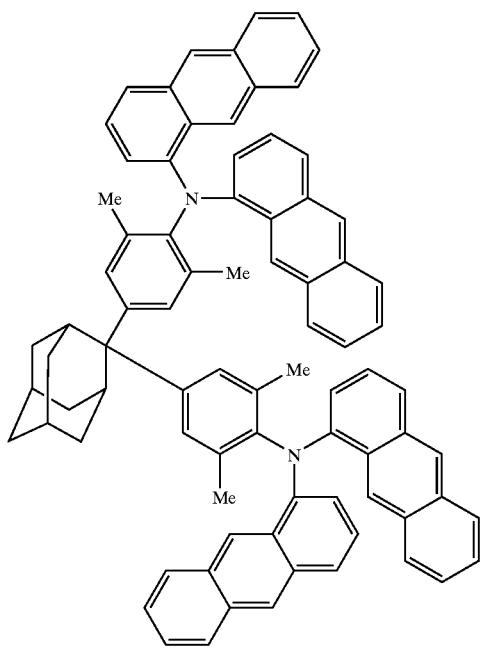
(a8)
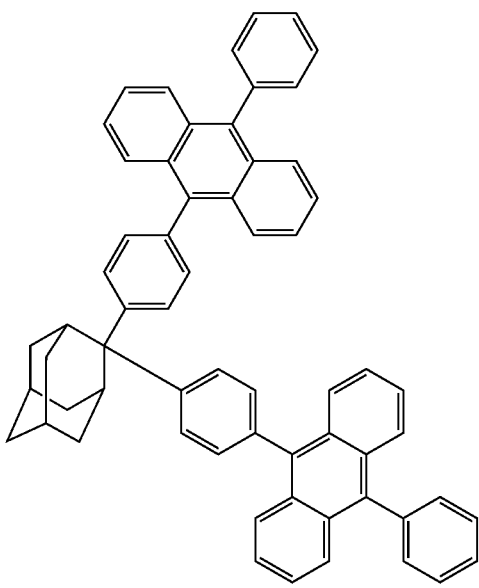
(a7)
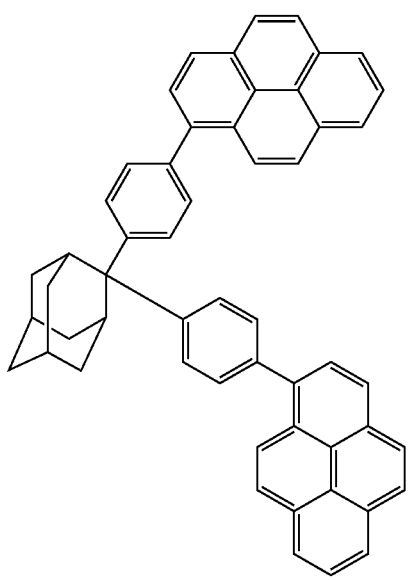
(a9)
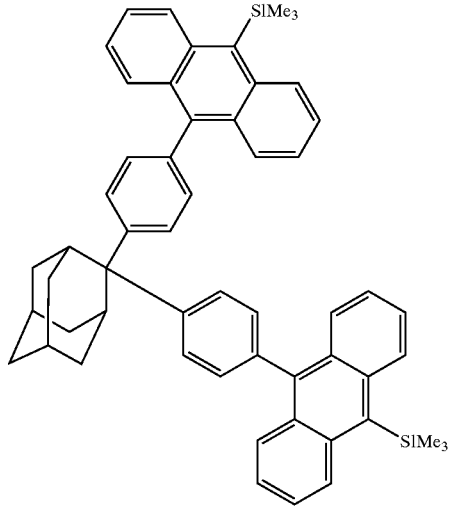

(a10)

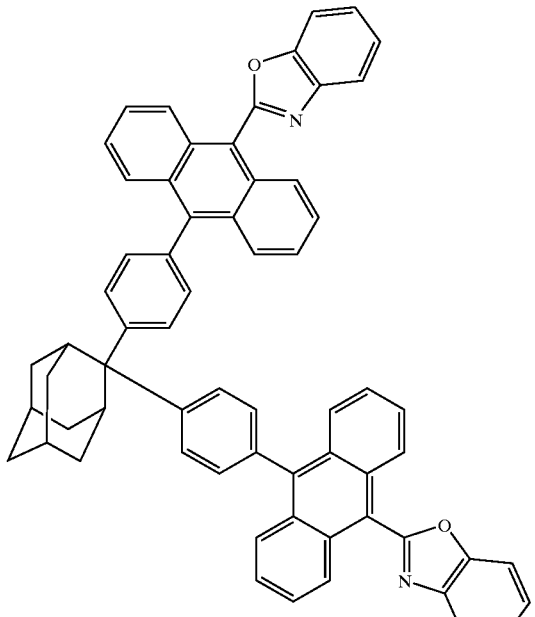

(a11)

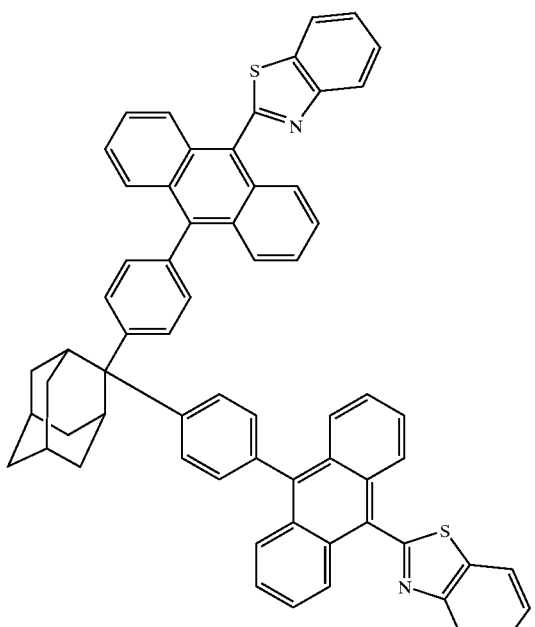

(a13)

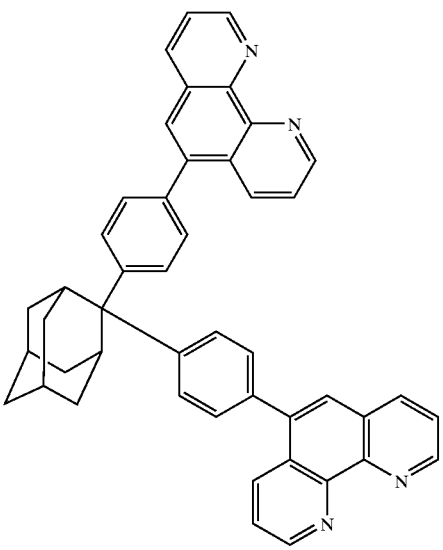

4. An electro luminescent element comprising at least one organic compound layer between electrodes, wherein,
   at least one said organic compound layer comprises an adamantane derivative represented by the chemical formula:

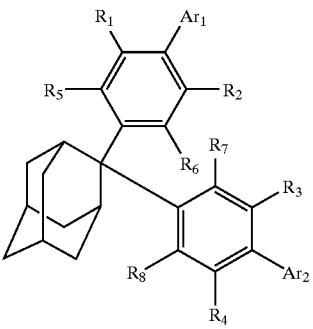

in which each of $R_1$ through $R_8$ represent substituents including hydrogen, and Ar1 and Ar2 represent functional units having a substituted or unsubstituted aryl skeleton which is directly bonded to the adamantane derivative, and wherein said organic compound layer has at least one property selected from the group consisting of a hole transporting ability, luminescence, and electron transporting ability.

5. The electro luminescent element according to claim 4, wherein said aryl skeleton is selected from the group of consisting of phenyl, naphthyl, and phenanthryl.

6. The electro luminescent element according to claim 4, wherein each of said functional units Ar1 and Ar2 is substituted by at least one functional group selected from the group consisting of alkyl group, aryl group, allyl group, alkene group, alkyne group, alkoxy group, hydroxy group, thiocarboxy group, dithiocarboxy group, sulfo group, sulfino group, sulfeno group, oxycarbonyl group, haloformyl group, carbamoyl group, hydrazinocarbonyl group, amidino group, cyano group, isocyano group, cyanato group, isocyanato group, thiocyanato group, isothiocyanato group, formyl group, oxo group, thioformyl group, thioxo group, mercapto group, amino group, imino group, hydrazino group, alkoxy group, aryloxy group, sulfide group, halogen, nitro group, and silyl group.

7. The electro luminescent element according to claim 4, wherein $R_1$ through $R_8$ represent substituents selected from the group consisting of alkyl group, aryl group, allyl group, alkene group, alkyne group, alkoxy group, hydroxy group, thiocarboxy group, dithiocarboxy group, sulfo group, sulfino group, sulfeno group, oxycarbonyl group, haloformyl group, carbamoyl group, hydrazinocarbonyl group, amidino group, cyano group, isocyano group, cyanato group, isocyanato group, thiocyanato group, isothiocyanato group, formyl group, oxo group, thioformyl group, thioxo group, mercapto group, amino group, imino group, hydrazino group, aryloxy group, sulfide group, halogen, nitro group, and silyl group.

8. An electro luminescent element comprising at least one organic compound layer between electrodes, wherein at least said one organic compound layer comprises a norbornane derivative represented by the chemical formula (a12):

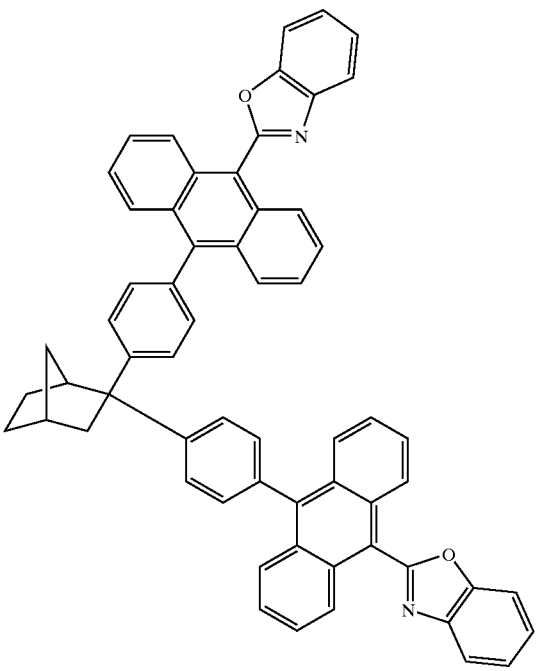

(a12)

* * * * *

UNITED STATES PATENT AND TRADEMARK OFFICE
CERTIFICATE OF CORRECTION

PATENT NO. : 6,777,111 B1
DATED : August 17, 2004
INVENTOR(S) : Tanaka et al.

It is certified that error appears in the above-identified patent and that said Letters Patent is hereby corrected as shown below:

<u>Title page</u>,
Item [73], Assignee, should read:
-- [73] Assignee: Kabushiki Kaisha Toyota Chuo Kenkyusho, Aichi-gun (JP) --

Signed and Sealed this

Twenty-first Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,777,111 B2
APPLICATION NO. : 09/632348
DATED : August 17, 2004
INVENTOR(S) : Hiromitsu Tanaka et al.

It is certified that error appears in the above-identified patent and that said Letters Patent is hereby corrected as shown below:

Column 40, line 31     "SIMe$_3$" should read --SiMe$_3$--;

Column 40, line 48     "SIMe$_3$" should read --SiMe$_3$--.

Signed and Sealed this

Twenty-third Day of January, 2007

JON W. DUDAS
*Director of the United States Patent and Trademark Office*